US011793770B2

(12) United States Patent
Stott et al.

(10) Patent No.: US 11,793,770 B2
(45) Date of Patent: *Oct. 24, 2023

(54) 7-OH-CANNABIDIOL (7-OH-CBD) AND/OR 7-OH-CANNABIDIVARIN (7-OH-CBDV) FOR USE IN THE TREATMENT OF EPILEPSY

(71) Applicant: GW Research Limited, Cambridge (GB)

(72) Inventors: Colin Stott, Cambridge (GB); Nick Jones, Cambridge (GB); Benjamin Whalley, Cambridge (GB); Gary Stephens, Reading (GB); Claire Williams, Reading (GB)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/472,000

(22) Filed: Sep. 10, 2021

(65) Prior Publication Data
US 2022/0062197 A1 Mar. 3, 2022

Related U.S. Application Data

(63) Continuation of application No. 16/591,702, filed on Oct. 3, 2019, now Pat. No. 11,147,776, which is a continuation of application No. 15/321,819, filed as application No. PCT/GB2015/051894 on Jun. 29, 2015, now abandoned.

(30) Foreign Application Priority Data

Jun. 27, 2014 (GB) ..................... 1411496

(51) Int. Cl.
A61K 31/05 (2006.01)
A61K 9/00 (2006.01)
A61K 9/08 (2006.01)
A61K 45/06 (2006.01)

(52) U.S. Cl.
CPC ............ *A61K 31/05* (2013.01); *A61K 9/0019* (2013.01); *A61K 9/08* (2013.01); *A61K 45/06* (2013.01)

(58) Field of Classification Search
CPC ..................................................... A61K 31/05
USPC ........................................................ 514/94
See application file for complete search history.

(56) References Cited

U.S. PATENT DOCUMENTS

| 6,949,582 | B1 | 9/2005  | Wallace          |
| 9,017,737 | B2 | 4/2015  | Kikuchi et al.   |
| 9,023,322 | B2 | 5/2015  | Van Damme et al. |
| 9,066,920 | B2 | 6/2015  | Whalley et al.   |
| 9,095,554 | B2 | 8/2015  | Lewis et al.     |
| 9,125,859 | B2 | 9/2015  | Whalley et al.   |
| 9,168,278 | B2 | 10/2015 | Guy et al.       |
| 9,259,449 | B2 | 2/2016  | Raderman         |
| 9,474,726 | B2 | 10/2016 | Guy et al.       |
| 9,517,989 | B2 | 12/2016 | Makriyannis et al. |
| 9,522,123 | B2 | 12/2016 | Whalley et al.   |
| 9,949,936 | B2 | 4/2018  | Guy et al.       |
| 9,949,937 | B2 | 4/2018  | Guy et al.       |
| 9,956,183 | B2 | 5/2018  | Guy et al.       |
| 9,956,184 | B2 | 5/2018  | Guy et al.       |
| 9,956,185 | B2 | 5/2018  | Guy et al.       |
| 9,956,186 | B2 | 5/2018  | Guy et al.       |
| 10,092,525 | B2 | 10/2018 | Guy et al.      |
| 10,111,840 | B2 | 10/2018 | Guy et al.      |
| 10,137,095 | B2 | 11/2018 | Guy et al.      |
| 10,583,096 | B2 | 3/2020  | Guy et al.      |
| 10,603,288 | B2 | 3/2020  | Guy et al.      |
| 10,709,671 | B2 | 7/2020  | Guy et al.      |
| 10,709,673 | B2 | 7/2020  | Guy et al.      |
| 10,709,674 | B2 | 7/2020  | Guy et al.      |
| 10,765,643 | B2 | 9/2020  | Guy et al.      |
| 10,807,777 | B2 | 10/2020 | Whittle         |
| 10,849,860 | B2 | 12/2020 | Guy et al.      |
| 10,918,608 | B2 | 2/2021  | Guy et al.      |
| 10,966,939 | B2 | 4/2021  | Guy et al.      |
| 11,065,209 | B2 | 7/2021  | Guy et al.      |
| 11,065,227 | B2 | 7/2021  | Stott et al.    |
| 11,096,905 | B2 | 8/2021  | Guy et al.      |
| 11,147,776 | B2 | 10/2021 | Stott et al.    |
| 11,147,783 | B2 | 10/2021 | Stott et al.    |
| 11,154,516 | B2 | 10/2021 | Guy et al.      |
| 11,154,517 | B2 | 10/2021 | Wright et al.   |
| 11,160,757 | B1 | 11/2021 | Wilkhu et al.   |
| 11,160,795 | B2 | 11/2021 | Guy et al.      |
| 11,207,292 | B2 | 12/2021 | Guy et al.      |
| 11,229,612 | B2 | 1/2022  | Wright et al.   |
| 2006/0039959 | A1 | 2/2006 | Wessling       |
| 2008/0119544 | A1 | 5/2008 | Guy et al.     |

(Continued)

FOREIGN PATENT DOCUMENTS

| EP | 2 448 637 B1 | 5/2012 |
| GB | 2384707 A | 8/2003 |

(Continued)

OTHER PUBLICATIONS

Statement of Opposition for EP10734541.5 mailed Dec. 5, 2014.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.
[No Author Listed], Cannabinoid. Wikipedia. Retrieved on Jul. 9, 2015 from https://en.wikipedia.org/wiki/Cannabinoid, 15 pages.

(Continued)

*Primary Examiner* — Taofiq A Solola
(74) *Attorney, Agent, or Firm* — COOLEY LLP

(57) ABSTRACT

The present invention relates to the use of 7-hydroxy-cannabidol (7-OH-CBD) and/or 7-hydroxy-cannabidivarin (7-OH-CBDV) in the treatment of epilepsy. Preferably the cannabinoid metabolites are isolated from plants to produce a highly purified extract or can be reproduced synthetically.

12 Claims, 1 Drawing Sheet

(56) References Cited

U.S. PATENT DOCUMENTS

| | | |
|---|---|---|
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0270845 A1 | 10/2012 | Bannister |
| 2013/0245110 A1 | 9/2013 | Guy et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0359755 A1 | 12/2015 | Guy et al. |
| 2015/0359756 A1 | 12/2015 | Guy et al. |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172940 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0209390 A1 | 7/2017 | Stott et al. |
| 2017/0246121 A1 | 8/2017 | Guy et al. |
| 2017/0273913 A1 | 9/2017 | Guy et al. |
| 2020/0297656 A1 | 9/2020 | Guy et al. |
| 2020/0352878 A1 | 11/2020 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2022/0000800 A1 | 1/2022 | Guy et al. |
| 2022/0008355 A1 | 1/2022 | Guy et al. |
| 2022/0023232 A1 | 1/2022 | Guy et al. |

FOREIGN PATENT DOCUMENTS

| | | |
|---|---|---|
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2478072 B | 12/2012 |
| GB | 2478074 B | 12/2012 |
| GB | 2492487 A | 1/2013 |
| GB | 2539472 A | 12/2016 |
| WO | WO 01/095899 A2 | 12/2001 |
| WO | WO 2002/064109 A2 | 8/2002 |
| WO | WO 2003/099302 A1 | 12/2003 |
| WO | WO 2004/016246 A1 | 2/2004 |
| WO | WO 2004/026802 A1 | 4/2004 |
| WO | WO 2006/054057 A2 | 5/2006 |
| WO | WO 2007/032962 A2 | 3/2007 |
| WO | WO 2007/083098 A1 | 7/2007 |
| WO | WO 2008/021394 A2 | 2/2008 |
| WO | WO 2008/094181 A3 | 8/2008 |
| WO | WO 2008/129258 A1 | 10/2008 |
| WO | WO 2008/146006 A1 | 12/2008 |
| WO | WO 2009/007697 A1 | 1/2009 |
| WO | WO 2009/020666 A1 | 2/2009 |
| WO | WO 2011/001169 A1 | 1/2011 |
| WO | WO 2012/033478 A1 | 3/2012 |
| WO | WO 2012/093255 A1 | 7/2012 |
| WO | WO 2013/032351 A1 | 3/2013 |
| WO | WO 2014/168131 A1 | 11/2013 |
| WO | WO 2015/142501 A1 | 9/2015 |
| WO | WO 2015/184127 A2 | 12/2015 |
| WO | WO 2015/193667 A1 | 12/2015 |

OTHER PUBLICATIONS

[No Author Listed] "Estimating the Maximum Safe Starting Dose in Initial Clinical Trials for Therapeutics in Adult Healthy Volunteers," FDA Guidance for Industry, Jul. 2005.

[No Author Listed] "GW Pharmaceuticals Announces Epidiolex(R) Receives Fast Track Designation from FDA for the Treatment of Dravet Syndrome," GW Pharmaceuticals Press Release dated Jun. 6, 2014.

[No Author Listed] "GW Pharmaceuticals Announces Physician Reports of Epidiolex® Treatment Effect in Children and Young Adults with Treatment-resistant epilepsy from Physician-Led Expanded Access Treatment Program," GW Pharmaceuticals Press Release dated Jun. 17, 2014.

[No Author Listed] GWPharm [online], "GW Pharmaceuticals Provides Update on Orphan Program in Childhood Epilepsy for Epidiolex®," GW Pharmaceuticals Press Release dated Nov. 15, 2013.

[No Author Listed] GW Pharmaceuticals Receives Orphan Drug Designation by FDA for Epidiolex® in the Treatment of Lennox-Gastaut Syndrome. GW Pharmaceuticals Press Release dated Feb. 28, 2014.

[No Author Listed] Salutaris Drops Buy Salutaris Drops—Salutaris Drops. Oct. 12, 2014. Last accessed on Jan. 20, 2017 from http://web.archive.org/web/20141012130255/http://salutarisdrops.com/buy-salutaris-drops/.

[No Author Listed] Salutaris Drops Cannabidiol for Aicardi Syndrome—Salutaris Drops. Oct. 12, 2014. Last accessed on Jan. 20, 2017 from http://web.archive.org/web/20141012220050/http://salutarisdrops.com/cannabidiol-aicardi-syndrome/.

Alger, "Not too excited? Thank your endocannabinoids," Neuron, 51(4):393-595 (2006).

Amada et al., "Cannabidivarin (CBDV) suppresses pentylenetetrazole (PTZ)-induced increases in epilepsy-related gene expression." PeerJ. Nov. 21, 2013;1:e214. doi:10.7717/peerj.214. eCollection Nov. 21, 2013.

Ames et al., "Anticonvulsant effect of cannabidiol," S Afr Med J., 69(1):14 (1986), 1 page.

Arain, "Pregabalin in the management of partial epilepsy," Neuropsychiatr Dis Treat., 5:407-413 (2009); Epub Aug. 20, 2009.

Avoli et al., "Cellular and molecular mechanisms of epilepsy in the human brain," Prog Neurobiol., 77(3):166-200 (2005).

Bakhsh et al., Miftaah-al-Khazaain. 1930: 607-8. Urdu. Exhibit 3.

Bancaud, "Proposal for Revised Clinical and Electroencephalographic Classification of Epileptic Seizures," Epilepsia, 22(4):489-501 (1981).

Bhatt et al. "Indigenous plants in traditional healthcare system in Kedarnath valley of western Himalaya," Indian J Tradit Knowl., 7(2):300-310 (2000).

Bhattacharyya et al., "Modulation of mediotemporal and ventrostriatal function in humans by Delta9-tetrahydrocannabinol: a neural basis for the effects of *Cannabis sativa* on learning and psychosis," Arch Gen Psychiatry, 66(4):442-451 (2009); doi:10.1001/archgenpsychiatry.2009.17.

Booth, "Legalization's opening of medical pot research is dream and nightmare," Denver Post, Dec. 14, 2013, 6 pages.

Bostanc et al. "The effects of octanol on penicillin induced epileptiform activity in rats: an in vivo study," Epilepsy Research, 71:188-194 (2006).

Brust et al., "Marijuana use and the risk of new onset seizures," Trans Am Clin Climatol Assoc., 103:176-181 (1992).

Carlini et al., "Hypnotic and antiepileptic effects of cannabidiol," J Clin Pharmacol., 21:417S-427S (1981).

Consroe et al. "Anticonvulsant drug antagonism of delta9tetrahydrocannabinol-induced seizures in rabbits," Res Commun Chem Pathol Pharmacol., 16(1):1-13 (1977).

(56) References Cited

OTHER PUBLICATIONS

Consroe et al. "Anticonvulsant interaction of cannabidiol and ethosuximide in rats," J Pharm Pharmacol., 29(8):500-501 (1977). doi:10.1111/j.2042-7158.1977.tb11378.x.

Consroe et al. "Anticonvulsant nature of marihuana smoking," JAMA, 234(3):306-307 (1975).

Consroe, P. & Wolkin, A., "Cannabidiol—antiepileptic drug comparisons and interactions in experimentally induced seizures in rats," J Pharmacol Exp Ther., 201(1):26-32 (1977).

Consroe et al. "Effects of cannabidiol on behavioral seizures caused by convulsant drugs or current in mice," Eur J Pharmacol., 83(3-4):293-298 (1982).

Cortesi et al. "Potential therapeutical effects of cannabidiol in children with pharmacoresistant epilepsy," Med Hypotheses, 68(4):920-921 2007). Epub Nov. 16, 2006.

Cunha et al. "Chronic administration of cannabidiol to healthy volunteers and epileptic patients." Pharmacology, 21(3):175-85 (1980).

Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci., 150:S162 (1997).

Dasa et al. "Key Attributes of TKDL: Ganja," Brhat Nighantu Ratnakara (Saligramanighantubhusanam), RS/4336, vol. IV. 1997:170, with English translation, 5 pages.

Davis et al. "Antiepileptic action of marijuana-active substances," Federation Proceedings, 8:284-285 (1949).

Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 29, 2003.

Deshpande et al., "Cannabinoid CB1 receptor antagonists cause status epilepticus-like activity in the hippocampal neuronal culture model of acquired epilepsy," Neurosci Lett. Jan. 2007; 411(1):11-6. Epub Nov. 15, 2006.

Dravet, "The core Dravet syndrome phenotype," Epilepsia. 52 Suppl 2:3-9. doi: 10.1111/j.1528-1167.2011.02994.x. (2011).

Eadie, "Shortcomings in the current treatment of epilepsy," Expert Rev Neurother, 12(12):1419-1427 (2012).

Eggers, "Temporal lobe epilepsy is a disease of faulty neuronal resonators rather than oscillators, and all seizures are provoked, usually by stress," Med Hypotheses., 69(6):1284-9 (2007).

Engel, "Report of the ILAE classification core group," Epilepsia, 47(9):1558-1568 (2006).

Ferdinand, et al., "Cannabis-psychosis pathway independent of other types of psychopathology," Schizophr Res., 79(2-3):289-295 (2005).

Fisher et al., "The impact of epilepsy from the patient's perspective I. Descriptions and subjective perceptions," Epilepsy Res, 41(1):39-51 (2000).

Gabor et al., "Lorazepam versus phenobarbital: Candidates for drug of choice for treatment of status epilepticus," J Epilepsy, 3(1):3-6 (1990).

Gardner, Comes Now Epidiolex. Oct. 23, 2013. Last accessed from http://theava.com/archives/24412 on Jan. 20, 2017.

Gastaut, "Clinical and electroencephalographical classification of epileptic seizures," Epilepsia, 11(1):102-113 (1970).

Geffrey et al. Cannabidiol (CBD) Treatment for Refractory Epilepsy in Tuberous Sclerosis Complex (TSC). American Epilepsy Society. 2014: Abstract 2.427. Last accessed from https://www.aesnet.org/meetings_events/annual_meeting_abstracts/view/1868979 on Jun. 30, 2015.

Gloss et al., "Cannabinoids for epilepsy," Cochrane Databse Syst Rev. Mar. 5, 2014;(3):CD009270/14651858.CD009270.pub3.

Gresham et al "Treating Lennox-Gastaut syndrome in epileptic pediatric patients with third generation rufinamide," Neuropsychiatr Dis Treat., 6:639-645, Oct. 5, 2010.

Gross et al. "Marijuana use and epilepsy: prevalence in patients of a tertiary care epilepsy center," Neurology, 62(11):2095-2097 (2004).

Hill, "Cannabidivarin is anticonvulsant in mouse and rat," Br J Pharmacol. Dec. 2012; 167(8):1629-42. doi:10.1111/j.1476-5381.2012.02207.x.

Hill, "Cannabidivarin-rich cannabis extracts are anticonvulsant in mouse and rat via a CB 1 receptor-independent mechanism," British Journal of Pharmacology, 170(3): 679-692 (2013).

Hill et al. "Δ9-Tetrahydrocannabivarin suppresses in vitro epileptiform and in vivo seizure activity in adult rats," Epilepsia, 51(8):1522-1532 (2010); doi: 10.1111/j.1528-1167.2010.02523.x. Epub Feb. 26, 2010.

Iuvone et al., "Neuroprotective effect of cannabidiol, a non-psychoactive component from *Cannabis sativa*, on beta-amyloid-induced toxicity in PC12 cells," J Neurochem., 89(1):134-141 (2004).

Jacobson, "Survey of Current Cannabidiol Use in Pediatric Treatment-Resistant Epilepsy," Poster, Apr. 22, 2013. Last accessed from http://www.thcint.com/uploads/1/9/3/7/19371199/cannabidiol_use_in_pediatric_epilepsy.dft on Jan. 20, 2017.

Jeavons et al., "Sodium valproate in treatment of epilepsy," Br Med J., 15; 2(5919):584-586 (1974).

Jones et al., "Cannabidiol displays antiepileptiform and antiseizure properties in vitro and in vivo," J. Pharmacol. Exp. Ther. Feb. 2010; 332(2):569-77. doi:10.1124/jpet.109.159145. Epub Nov. 11, 2009.

Jones et al., "Cannabidiol exerts anti-convulsant effects in animal models of temporal lobes and partial seizures," Seizure. Jun. 2012; 21(5):344-52. doi: 10.1016/j.seizure.2012.03.001. Epub Apr. 19, 2012.

Joy et al., Marijuana and Medicine. Assessing the Science Bse. National Academy Press., Washington, D.C. 1999, 170 pages.

Karler et al, "The cannabinoids as potential antiepileptics," J Clin Pharmacol, 21(8-9 Suppl): 437S-447S (1981).

Khan et al., "Key Attributes of TKDL: Laooq-e-Quinnab/Barai Zeequn-Nafs," Khazaain-al-Advia, 1911 (with English translation), 2 pages.

Khan et al., Key Attributes of TKDL: Nushka-e-Qutoor, Muheet-e-Azam, 1887 (with English translation), 2 pages.

Khan et al., "Key Attributes of TKDL: Sufoof-e-Qinnab Barae Waja," Khazaain-al-Adiva, 1911, (with English translation), 5 pages.

Khan et al., "Key Attributes of TKDL: Usaara-e-Qinnab Barai Qoolanj," Khazaain-al-Advia, 1911 (with English translation), 6 pages.

Khan et al., "Key Attributes of TKDL: Zimad-e-Qinnab," Khazaain-al-Adiva, 1911 (with English translation), 5 pages.

Klitgaard et al., "Electrophysiological, neurochemical and regional effects of levetiracetam in the rat pilocarpine model of temporal lobe epilepsy," Seizure, 12(2):92-100 (2003).

Kramer et al., "Febrile infection-related epilepsy syndrome (FIRES): pathogenesis, treatment, and outcome: a multicenter study on 77 children," Epilepsia, 52(11):1956-1965 (2011); doi: 10.1111/j.1528-1167.2011.03250.x. Epub Aug. 29, 2011.

Kwan et al., "Definition of drug resistant epilepsy: consensus proposal by the ad hoc Task Force of the ILAE Commission on Therapeutic Strategies," Epilepsia, 51(6):1069-1077 (2010); doi:10.1111/j.1528-1167.2009.02397.x.

Long et al., "The pharmacological actions of cannabidiol," Drugs of the Future, 30(7):747-53 (2005).

Lutz, "On-demand activation of the endocannabinoid system in the control of neuronal excitability and epileptiform seizures," Biochem Pharmacol, 68(9):1691-1698 (2004).

Maa et al., "The case for medical marijuana in epilepsy," Epilepsia, 55(6):783-786 (2014); doi: 10.1111/epi.12610.

Mackie, "Cannabinoid receptors as therapeutic targets," Annu Rev Pharmacol Toxicol., 46:101-22 (2006).

Majoosi et al., "Key Attributes of TKDL: Saoot Baraae Sara," Kaamil-al-Sena'ah, Central Council for Research in Unani Medicine, 2005 (with English translation), 2 pages.

McCormick et al., "On the cellular and network bases of epileptic seizures," Annu Rev Physiol, 63:815-846 (2001).

Mechoulam et al., "Toward drugs derived from cannabis," Naturwissenschaften, 65(4):174-179 (1978).

Merlis, "Proposal for an International Classification of the Epilepsies," Epilepsia, 11:114-119 (1970).

(56) References Cited

OTHER PUBLICATIONS

Ng et al., "Illicit drug use and the risk of new-onset seizures," Am J Epidemiol., 132(1):47-57 (1990).
Obay et al., "Antiepileptic effects of ghrelin on pentylenetetrazole-induced seizures in rats," Peptides, 28(6):1214-1219. Epub Apr. 19, 2007.
Pelliccia et al.., "Treatment with CBD in oily solution of drug-resistant pediatric epilepsies," 2005 Congress on Cannabis and the Cannabinoids, Leiden, The Netherlands: International Association for Cannabis as Medicine, 2005, p. 14.
Pereira et al., "Study pharmacologic of the GABAergic and glutamatergic drugs on seizures and status epilepticus induced by pilocarpine in adult Wistar rats," Neurosci Lett.., 419(3):253-257 (2007). Epub Apr. 13, 2007.
Pertwee, "Cannabinoid receptor ligands: clinical and neuropharmacological considerations, relevant to future drug discovery and development," Expert Opin Investig Drugs, 9(7):1553-1571 (2000).
Pohl et al., "Effects of flunarizine on Metrazol-induced seizures in developing rats," Epilepsy, 1(5):302-305 (1987).
Porter et al., "Report of a parent survey of cannabidiol-enriched cannabis use in pediatric treatment-resistant epilepsy," Epilepsy Behav., 29(3):574-577 (2013).
Press et al., "Parenteral reporting of response to oral cannabis extracts for treatment of refractory epilepsy," Epilepsy Behav, 45:49-52 (2015).
Rauca et al., "The role of superoxide dismutase and alpha-tocopherol in the development of seizures and kindling induced by pentylenetetrazol—influence of the radical scavenger alpha-phenyl-N-tert-butyl nitrone," Brain Research, 1009(1-2):203-212 (2004).
Resstel et al. "5-HT1A receptors are involved in the cannabidiol-induced attenuation of behavioural and cardiovascular responses to acute restraint stress in rats," Br J Pharmacol., 156(1):181-188 (2009).
Rosenthaler et al., "Differences in receptor binding affinity of several phytocannabinoids do not explain their effects on neural cell cultures," Neurotoxicology and Teratology, 46, 2014, 49-56.
Sadanandasarma et al., "Key Attributes of TKDL: Suddha Bhanga Visista Gunah Aur Matra," Rasatarangini 11th Ed., 720-723 (with English translation), 8 pages.
Sander, "The epidemiology of epilepsy revisited," Curr Opin Neural, 16(2):165-170 (2003).
Sastri et al., "Key Attributes of TKDL: Vijaya Kalpah (Apasmaranasaka)," Anandakandam 1st ed., 1952:241 (with English translation), 5 pages.
Scuderi et al., "Cannabidiol in medicine: a review of its therapeutic potential in CNS disorders," Phytother Res., 23(5):597-602 (2009).
Stott et al., "Cannabinoids for the pharmaceutical industry," Euphytica, 140:83-93 (2004).
Swann et al., "The effects of seizures on the connectivity and circuitry of the developing brain," Ment Retard Dev Disabil Res Rev., 10(2):96-100 (2004).
Thomas et al., "Evidence that the plant cannabinoid Delta9-tetrahydrocannabivarin is a cannabinoid CB1 and CB2 receptor antagonist," Br J Pharmacol., 146(7):917-926 (2005).
Thurman et al., "Standards for epidemiologic studies and surveillance of epilepsy," Epilepsia, 52 (Suppl 7):2-26 (2011).
Trembly et al., "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Usami et al., "Synthesis and pharmacological evaluation in mice of halogenated cannabidiol derivatives," Chem Pharm Bull (Tokyo), 47(11):1641-1645 (1999).
Vollner et al., "Haschisch XX+ [Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Assessment of the role of CB 1 receptors in cannabinoid anticonvulsant effects," Eur J Pharmacol., 428(1):51-57 (2001).
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.
Wingerchuk, "Cannabis for medical purposes: cultivating science, weeding out the fiction," Lancet, 364:315-316 (2004).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).

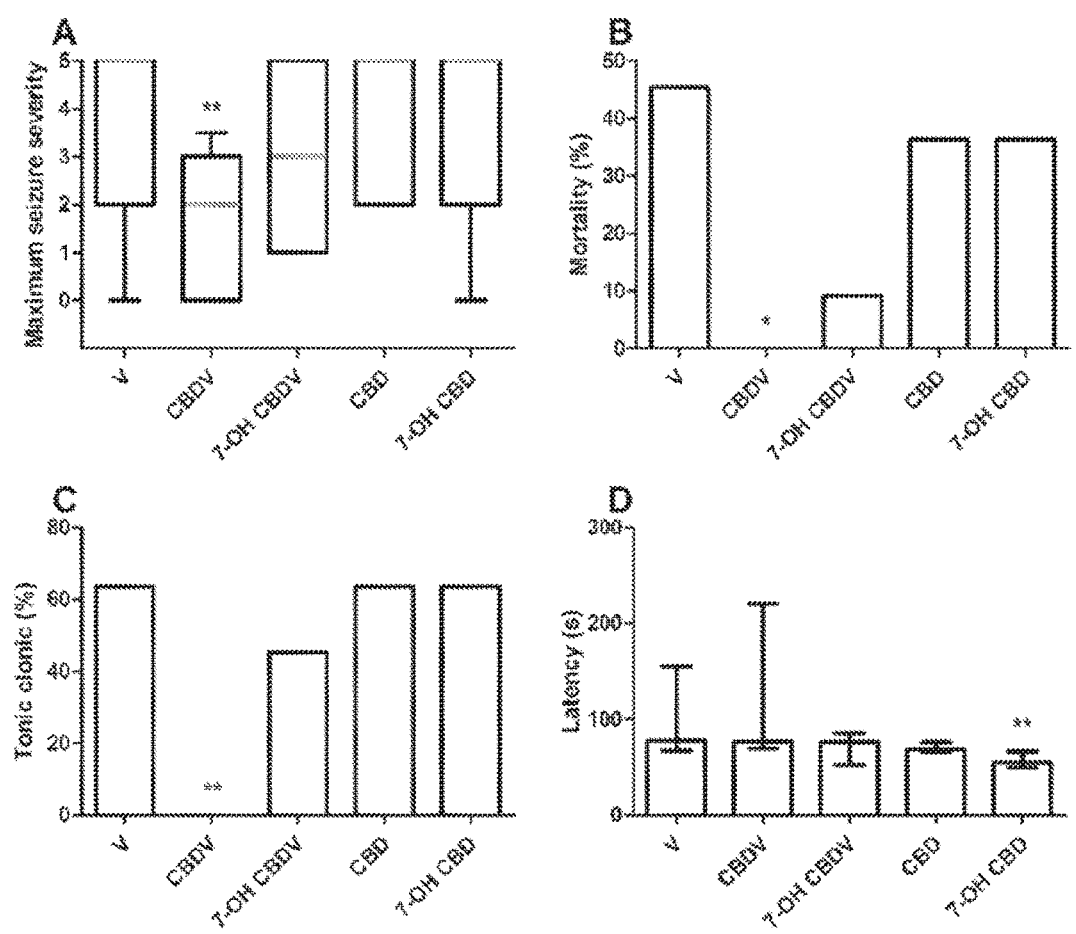
CBDV and CBD, and their 7-OH metabolites in the PTZ model of acute seizure

7-OH-CANNABIDIOL (7-OH-CBD) AND/OR 7-OH-CANNABIDIVARIN (7-OH-CBDV) FOR USE IN THE TREATMENT OF EPILEPSY

RELATED APPLICATIONS

This application is a Continuation of U.S. application Ser. No. 16/591,702, filed Oct. 3, 2019, which is a Continuation of U.S. application Ser. No. 15/321,819, filed Dec. 23, 2016, which is a national stage filing under 35 U.S.C. § 371 of International Application No. PCT/GB2015/051894, filed Jun. 29, 2015, which claims the benefit of GB Serial No. 1411496.1, filed Jun. 27, 2014, the entire disclosure of each of which is incorporated by reference herein in its entirety.

The present invention relates to the use of 7-hydroxy-cannabidol (7-OH-CBD) and/or 7-hydroxy-cannabidivarin (7-OH-CBDV) in the treatment of epilepsy.

Preferably the cannabinoid metabolites are isolated from plants to produce a highly purified extract or can be reproduced synthetically.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from "treatment-resistant epilepsy" (TRE).

There are several different types of AED available to treat epilepsy, some of the most common AED defined by their mechanisms of action are described in the following tables:

| Narrow-spectrum AED | Mechanism |
| --- | --- |
| Phenytoin | Sodium channel |
| Phenobarbital | GABA/Calcium channel |
| Carbamazepine | Sodium channel |
| Oxcarbazepine | Sodium channel |
| Gabapentin | Calcium channel |
| Pregabalin | Calcium channel |
| Lacosamide | Sodium channel |
| Vigabatrin | GABA |

| Broad-spectrum AED | Mechanism |
| --- | --- |
| Valproic acid | GABA/Sodium channel |
| Lamotrigine | Sodium channel |
| Topiramate | GABA/Sodium channel |
| Zonisamide | GABA/Calcium/Sodium channel |
| Levetiracetam | Calcium channel |
| Clonazepam | GABA |
| Rufinamide | Sodium channel |

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

Childhood epilepsy refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

Examples of AED Used Specifically in Childhood Epilepsy

| AED | Mechanism |
| --- | --- |
| Clobazam | GABA |
| Stiripentol | GABA |

The International League Against Epilepsy (ILAE) in 2011 have reclassified the old terms of "general" and "partial" seizures". The new term "generalized seizure" refers to seizures conceptualized as originating at some point within the brain and rapidly engaging bilaterally distributed networks.

The new term "focal seizure" now refers to seizures conceptualized as originating at some point within the brain and being limited to one hemisphere.

The etiology of epilepsy has also been reclassified by the ILAE as being of genetic origin; structural or metabolic origin; or of unknown origin.

There is also now no specific classification for focal seizure types, therefore the terms complex partial and simple partial seizure are no longer in use.

There are several different animal models that can be used to test the efficacy of compounds as anti-convulsants. These include the pentylenetetrazole-induced (PTZ) model of generalised seizures and the Maximal Electroshock (MES) model of generalised seizures.

Over the past forty years there have been a number of animal studies on the use of the non-psychoactive cannabinoid cannabidiol (CBD) to treat seizures. For example, Consroe et al., (1982) determined that CBD was able to prevent seizures in mice after administration of pro-convulsant drugs or an electric current.

Studies in epileptic adults have also occurred in the past forty years with CBD. Cunha et al. reported that administration of CBD to eight adult patients with generalized epilepsy resulted in a marked reduction of seizures in 4 of the patients (Cunha et al., 1980).

A study in 1978 provided 200 mg/day of pure CBD to four adult patients, two of the four patients became seizure free, whereas in the remainder seizure frequency was unchanged (Mechoulam and Carlini, 1978).

Carlini et al. in 1981 described a further study where CBD was provided to healthy volunteers, insomniacs and epileptic patients. Seven out of the eight epileptic patients described an improvement in their condition.

In contrast to the studies described above, an open label study reported that 200 mg/day of pure CBD was ineffective in controlling seizures in twelve institutionalized adult patients (Ames and Cridland, 1986).

In the past forty years of research there have been over thirty drugs approved for the treatment of epilepsy none of which are cannabinoids. Indeed, there appears to have been a prejudice against cannabinoids, possible due to the scheduled nature of these compounds and/or the fact that THC, which is a known psychoactive, has been ascribed as a pro-convulsant (Consroe et al., 1977).

More recently the applicant has discovered that the cannabinoids CBD and CBDV are effective in animal models of epilepsy. For example EP 2,448,637 describes the use of CBD in the treatment of partial seizures and WO 2011/121351 describes the use of CBDV in the treatment of epilepsy. Hill et al. (2012) and Amada et al. (2013) both also describe the use of CBDV in the treatment of epilepsy. Jones et al. (2012) describes the anti-convulsant activity of CBD in animal models.

Furthermore GB 2495118 describes the use of a pharmaceutical composition comprising a combination of CBDV and CBD.

The synthetic production of the metabolite of CBD, 7-hydroxy-cannabidiol, (7-OH CBD) is disclosed in WO 01/95899 in addition to many other CBD derivatives. The compound was tested in a model of inflammation and found to be effective. The application goes on to suggest that the compound may be of use as an analgesic, anti-anxiety, anti-convulsant, neuroprotective, anti-psychotic and anti-inflammatory based on the mechanisms the compound displays in the model of inflammation. However no data is presented to support the use of 7-OH-CBD as an anti-convulsant.

To date there have been no studies into the anti-convulsant effect of metabolites of CBD and CBDV.

Surprisingly, it has now been found that a metabolite of CBD, 7-hydroxy-cannabidiol, (7-OH CBD) and a metabolite of CBD, 7-hydroxy-cannabidivarin, (7-OH CBDV) are effective in the treatment of epilepsy. The metabolites appear to be more effective than their parent compounds in certain aspects of seizure control.

BRIEF SUMMARY OF THE DISCLOSURE

In accordance with a first aspect of the present invention there is provided 7-hydroxy-cannabidivarin (7-OH-CBDV) in a pure, isolated or synthetic form for use as a medicament.

In accordance with a second aspect of the present invention there is provided 7-hydroxy-cannabidivarin (7-OH-CBDV) in a pure, isolated or synthetic form for use in the treatment of epilepsy.

In accordance with a third aspect of the present invention there is provided 7-hydroxy-cannabidol (7-OH-CBD) in a pure, isolated or synthetic form for use in the treatment of epilepsy.

In one embodiment the 7-hydroxy-cannabidivarin (7-OH-CBDV) in a pure, isolated or synthetic form is used in combination with 7-hydroxy-cannabidol (7-OH-CBD) in a pure, isolated or synthetic form.

In accordance with a fourth aspect of the present invention there is provided a pharmaceutical composition comprising 7-hydroxy-cannabidivarin (7-OH-CBDV) and/or 7-hydroxy-cannabidol (7-OH-CBD) with a pharmaceutically acceptable carrier.

In accordance with a fifth aspect of the present invention there is provided a pharmaceutical composition comprising 7-hydroxy-cannabidivarin (7-OH-CBDV) and/or 7-hydroxy-cannabidol (7-OH-CBD) with a pharmaceutically acceptable carrier for use in the treatment of epilepsy.

In one embodiment the 7-hydroxy-cannabidol (7-OH-CBD) and/or 7-hydroxy-cannabidivarin (7-OH-CBDV) are used in combination with one or more concomitant anti-epileptic drugs (AED).

Preferably the one or more AED is selected from the group consisting of: clobazam; levetiracetam; topiramate; stiripentol; phenobarbital; lacsamide; valproic acid; zonisamide; perampanel; and fosphenytoin.

Preferably the dose of 7-OH-CBD and/or the 7-OH-CBDV is between 1 and 2000 mg/kg.

Preferably the 7-OH-CBDV may be formulated for administration separately, sequentially or simultaneously with the 7-OH-CBD or the combination may be provided in a single dosage form.

It is envisaged that the composition be administered as an oral liquid solution. Other modes of administration including solids, semi-solids, gels, sprays, aerosols, inhalers, vaporisers, enemas and suppositories are alternative administration forms. Such medicaments could be administered via the oral, buccal, sublingual, respiratory, nasal and distal rectum route.

In accordance with a sixth aspect of the present invention there is provided a method of treating epilepsy comprising administering a therapeutically effective amount of 7-hydroxy-cannabidiol (7-OH-CBD) and/or 7-hydroxy-cannabidivarin (7-OH-CBDV) to a subject in need thereof.

BRIEF DESCRIPTION OF THE DRAWINGS

Embodiments of the invention are further described hereinafter with reference to the accompanying drawings, in which:

FIG. 1 shows CBDV and CBD, and their 7-OH metabolites in the PTZ model of acute seizure.

LEGEND TO THE FIGURES

FIG. 1. CBDV and 7-OH CBDV were dosed at 200 mg/kg, and CBD and 7-OH CBD were dosed at 100 mg/kg (A) Maximum observed seizure severity (median severity in grey, box represents interquartile range, whiskers represent maxima and minima; Kruskal-Wallis test, with a post-hoc Mann-Whitney U) (B) Mortality (Chi-squared test, with a post-hoc Fisher exact) (C) Animals exhibiting tonic-clonic seizures (Chi-squared test, with a post-hoc Fisher exact) (D) Latency to seizure onset (median with interquartile range; Kruskal-Wallis test, with a post-hoc Mann-Whitney U). n=11 for each dose, *=$p \leq 0.05$, **=$p \leq 0.01$.

Definitions

Definitions of some of the terms used to describe the invention are detailed below:

The cannabinoids described in the present application are listed below along with their standard abbreviations.

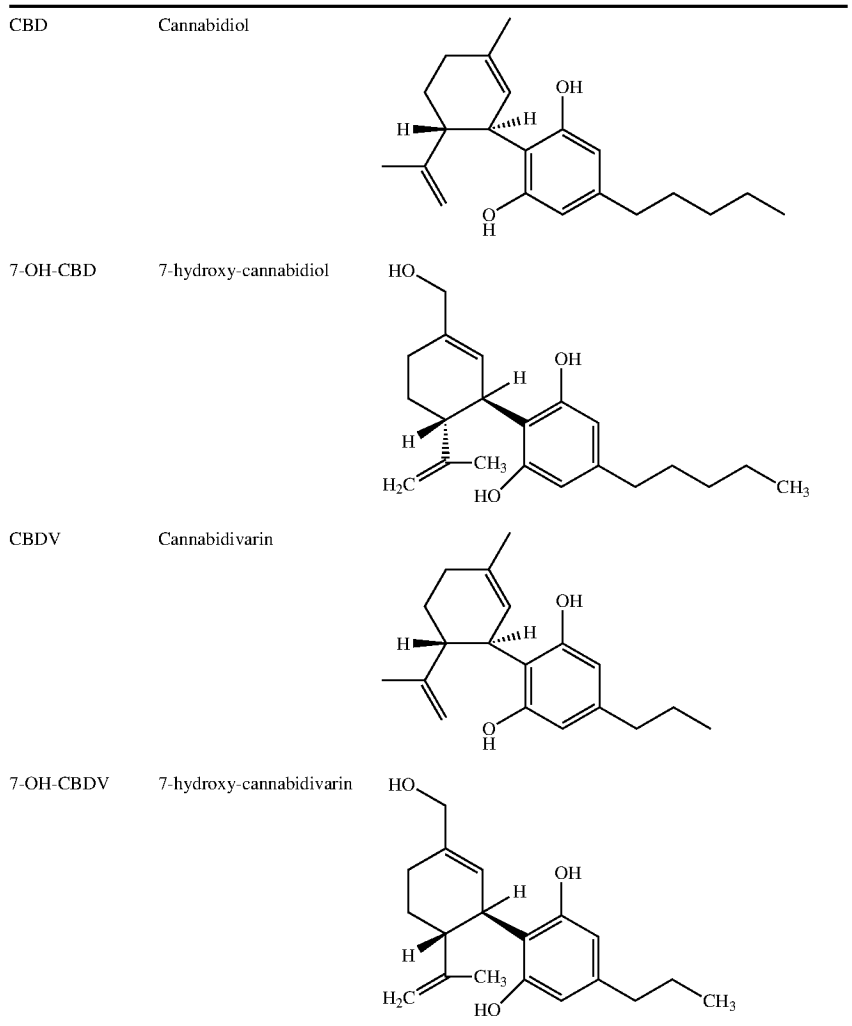

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Cannabinoid metabolites" are metabolites from cannabinoids that originate when the parent cannabinoid is metabolised or broken down. The cannabinoid metabolites can be isolated from plants to produce a highly purified extract or can be reproduced synthetically.

"Highly purified cannabinoid metabolites" are defined as cannabinoids that have been extracted from the cannabis plant and purified to the extent that other cannabinoids and non-cannabinoid components that are co-extracted with the cannabinoids have been removed, such that the highly purified cannabinoid is greater than 90%, more preferably greater than 95%, most preferably greater than 98% (w/w) pure.

The cannabinoid metabolites may be manufactured synthetically and/or produced from the parent cannabinoid by enzymatic means.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

The human dose equivalent (HED) can be estimated using the following formula:

$$HED = \text{Animal dose (mg/kg) multiplied by } \frac{\text{Animal } K_m}{\text{Human } K_m}$$

The $K_m$ for a rat is 6 and the $K_m$ for a human is 37.

Thus, for a human of approximately 60 Kg a 200 mg/Kg dose in rat would equate to a human daily dose of about 2000 mg.

DETAILED DESCRIPTION

The following Examples describe for the first time the anti-convulsant activity of the metabolites of CBD, namely 7-OH-CBD and CBDV, namely, 7-OH-CBDV.

Example 1: Efficacy of 7-Hydroxy Cannabidiol (7-OH-CBD) and 7-Hydroxy Cannabidivarin (7-OH-CBDV) in the PTZ Model of Seizure Materials and Methods Compounds:

The compounds 7-OH CBD and 7-OH-CBDV have never been tested in a model of epilepsy and as such the effects were examined at one dose level in order to determine efficacy.

The hydroxy-metabolites of CBD and CBDV were also tested against their parent cannabinoids which were used as positive controls. The table below details the doses used in this study.

| Compound | Dose (mg/kg) |
|---|---|
| Vehicle | — |
| CBDV | 200 |
| 7-OH-CBDV | 200 |
| CBD | 100 |
| 7-OH CBD | 100 |

General Methodology for PTZ Model

Animals

Male Wistar rats (P24-29; 75-110 g) were used to assess the effects of the cannabinoids listed above on the PTZ model of generalised seizures. Animals were habituated to the test environment, cages, injection protocol and handling prior to experimentation. Animals were housed in a room at 21° C. on a 12 hour light: dark cycle (lights on 0900) in 50% humidity, with free access to food and water.

Experimental Setup

Five 6 L Perspex (RTM) tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux (RTM) scripts were used to encode video files into a suitable format for further offline analysis Experimental Protocols On the day of testing, animals received an IP injection with either the cannabinoids (or a matched volume of the cannabinoids vehicle (1:1:18 ethanol:Cremophor: 0.9% w/v NaCl solution), which served as the negative control group. Animals were then observed for 30 mins, after which time they received an IP injection of 70 or 80 mg/kg PTZ. Negative vehicle controls were performed in parallel with cannabinoid-dosed subjects. After receiving a dose of PTZ, animals were observed and videoed to determine the severity of seizure and latency to several seizure behaviour types (see in vivo analysis, below). Animals were filmed for half an hour after last sign of seizure, and then returned to their cage.

In Vivo Analysis

Animals were observed during experimental procedures, but all analysis was performed offline on recorded video files using The Observer behavioural analysis software (Noldus, Netherlands). A seizure severity scoring system was used to determine the levels of seizure experienced by subjects (Table 1). All signs of seizure were detailed for all animals.

TABLE 1

| Seizure severity scoring scale | | |
|---|---|---|
| Seizure score | Behavioural expression | Righting reflex |
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |
| 6 | Death | |

Latency from Injection of PTZ to Specific Indicators of Seizure Development:

The latency (in seconds) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale above.

Percentage Mortality:

The percentage of animals within an experimental group that died as a result of PTZ-induced seizures. A score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean±S.E.M. for each experimental group.

Statistics:

Differences in latencies and durations were assessed by one-way analysis of variance (ANOVA) with post-hoc Tukey's test. $P \leq 0.05$ was considered significant.

Results

FIG. 1A shows that treatment with all of the compounds, both parents and metabolites resulted in a decrease the observed maximum seizure severity. CBDV significantly reduced seizure severity ($p \leq 0.01$).

FIG. 1B shows that CBDV and 7-OH-CBDV had a significant effect on mortality of the animals. There was also a reduction in mortality observed for CBD and 7-OH-CBD.

FIG. 1C demonstrates that the incidence of tonic clonic seizures was significantly reduced by CBDV and to a lesser extent 7-OH-CBDV.

FIG. 1D demonstrates that the latency to the onset of seizures was also affected by the administration of cannabinoids. Indeed 7-OH CBD significantly reduced the latency to seizure onset ($p \leq 0.01$).

Conclusions

These results demonstrate that both 7-OH-CBD and 7-OH-CBDV show anti-convulsant action in the PTZ model of acute seizure.

Furthermore the ability 7-OH-CBD to significantly reduce the latency to onset of seizures and of 7-OH-CBDV to significantly reduce the median seizure severity, from 5 to 3 are remarkable as these data infer that the metabolites may be more effective than their parent compounds in certain aspects of seizure control.

The fact that the 7-OH-CBD and 7-OH-CBDV appear to be more potent than their parent cannabinoids, CBD and CBDV respectively, means that lower doses of the metabolites may be used in the treatment of epilepsy.

Example 2: Efficacy of 7-Hydroxy Cannabidivarin (7-OH-CBDV) in the Maximal Electroshock (MES) Model of Seizure Preparation of Test and Reference Compounds The vehicle used in this study was 2:1:17 (ethanol:Cremophor:0.9% w/v NaCl). The test compound used was 7-OH-CBDV. This was made to a solution at the highest concentration; then dissolved in ethanol before combination with Cremophor and 0.9% NaCl in the proportion described above. The 7-OH-CBDV was administered intraperitoneally at a volume of 10 ml/kg body weight.

Test System

Animal Species/Strain: Mouse/ICR, Microbiological grade: SPF, Inc. Sex: male, Age (at time of testing): 5-7 weeks old, Number of animals: about 5 animals per group. Temperature: 23±2° C., Humidity: 60±10%, Light conditions: 7 AM to 7 PM for the light period, 7 PM to 7 AM for the dark period. Chow and water: Free access to CRF-1 (Oriental Yeast Co, Ltd) and tap water.

Experimental Procedures

One day before each experiment, mice were weighed and randomized into several groups in each test. On the morning of the experiment day, body weight was measured in order to calculate the administration volume of each animal. Vehicle, 7-OH-CBDV or CBDV was interperitoneally administered 30 minutes before electric stimuli. Maximal electroshock seizures (MES) in mice was induced by a stimulator (UGO BASILE ECT UNIT 7801, Italia) using a current of 30 mA delivered with a pulse frequency of 100 Hz for 200 msec through earlap electrodes. The mice were observed for 10 seconds and the incidence of tonic hindlimb extension was noted.

Statistical Analysis

All statistical analyses were performed using SAS Software for Windows, Release 9.1. The difference of the number (hindlimb extension or deaths) in each group was assessed using two-tailed Fisher's exact test. The differences were considered statistically significant, when the p value was less than 0.05.

Results

Table 2 below demonstrates that the data obtained for the 7-OH-CBDV was statistically significant when compared to vehicle. Similarly to the parent compound, CBDV, 7-OH-CBDV at both doses produced a decrease in 90% of tonic clonic convulsions.

TABLE 2

Percentage decrease in tonic clonic convulsions

| Compound (dose) | Percentage decrease in tonic clonic convulsions compared with vehicle |
| --- | --- |
| Vehicle | — |
| 7-OH-CBDV (150 mg/kg i.p.) | 90% *** |
| 7-OH-CBDV (200 mg/kg i.p.) | 90% *** |
| CBDV (200 mg/kg i.p.) | 82% *** |

*** — = p < 0.001

Conclusion

These data further demonstrate the surprising ability of the primary metabolite of CBDV, 7-OH-CBDV to produce anti-convulsant effects.

REFERENCES

Amada et al. (2013) PeerJ, 2013, pages 1-18 "Cannabidivarin (CBDV) suppresses pentylenetetrazole (PTZ)-induced increases in epilepsy-related gene expression."

Ames F R and Cridland S (1986). "Anticonvulsant effects of cannabidiol." S Afr Med J 69:14.

Carlini et al. (1981) Journal of Clinical Pharmacology, vol. 21, No. 8/9, 1981, pages 417S-427S "Hypnotic and antiepileptic effects of cannabidiol."

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Hill et al. (2012) British Journal of Pharmacology, vol. 167, No. 8, 2012, pages 1629-1642 "Cannabidivarin is anti-convulsant in mouse and rat."

Jones et al. (2012) Seizure, vol. 21, No. 5, 2012, pages 344-352 "Cannabidiol exerts anti-convulsant effects in animal models of temporal lobe and partial seizures."

Mechoulam R and Carlini E A (1978). "Toward drugs derived from cannabis." Die naturwissenschaften 65:174-9.

The invention claimed is:

1. A method of treating myoclonic jerks in a subject with epilepsy comprising administering a therapeutically effective amount of 7-hydroxy-cannabidiol (7-OH-CBD), thereby treating myoclonic jerks.

2. The method of claim 1, wherein the 7-OH-CBD is in a pure, isolated or synthetic form.

3. The method of claim 1, further comprising administering to the subject a therapeutically effective amount of 7-hydroxy-cannabidivarin (7-OH-CBDV).

4. The method of claim 1, wherein the 7-OH-CBD is administered as a pharmaceutical composition comprising the 7-OH-CBD with a pharmaceutically acceptable carrier.

5. The method of claim 1, further comprising administering to the subject one or more concomitant anti-epileptic drugs (AED).

6. The method of claim 5, wherein the one or more AED is selected from the group consisting of: clobazam; levetiracetam; topiramate; stiripentol; phenobarbital; lacsamide; valproic acid; zonisamide; perampanel; and fosphenytoin.

7. The method of claim 1, wherein the dose of 7-OH-CBD is between 1 and 2000 mg/kg.

8. The method of claim 3, wherein the 7-OH-CBD is formulated for administration separately, sequentially or simultaneously with the 7-OH-CBDV or the combination is provided in a single dosage form.

9. The method of claim 3, wherein the 7-OH-CBDV is in a pure, isolated or synthetic form.

10. The method of claim 3, wherein the dose of 7-OH-CBDV is between 1 and 2000 mg/kg.

11. The method of claim 3, wherein the pharmaceutical composition further comprises 7-hydroxy-cannabidivarin (7-OH-CBDV).

12. The method of claim 1, wherein the 7-OH-CBD is administered in an oral solution comprising the 7-OH-CBD and a pharmaceutically acceptable carrier.

* * * * *